US009140601B2

(12) United States Patent
Mehendale et al.

(10) Patent No.: US 9,140,601 B2
(45) Date of Patent: Sep. 22, 2015

(54) POSITION SENSITIVE DETECTION OPTIMIZATION

(75) Inventors: Manjusha Mehendale, Morristown, NJ (US); Michael Kotelyanskii, Chatham, NJ (US); Priya Mukundhan, Lake Hopatcong, NJ (US); Michael Colgan, Flanders, NJ (US); Wei Zhou, Minnetonka, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 13/982,109

(22) PCT Filed: Jan. 27, 2012

(86) PCT No.: PCT/US2012/022911
§ 371 (c)(1),
(2), (4) Date: Nov. 20, 2013

(87) PCT Pub. No.: WO2012/103440
PCT Pub. Date: Aug. 2, 2012

(65) Prior Publication Data
US 2014/0103188 A1   Apr. 17, 2014

Related U.S. Application Data

(60) Provisional application No. 61/462,154, filed on Jan. 28, 2011.

(51) Int. Cl.
*G01N 21/00*  (2006.01)
*G01J 1/04*  (2006.01)
(Continued)

(52) U.S. Cl.
CPC ............... *G01J 1/0448* (2013.01); *G01N 21/47* (2013.01); *G01N 21/55* (2013.01); *G01N 21/1702* (2013.01); *G01N 21/9501* (2013.01)

(58) Field of Classification Search
CPC ... G01J 1/0448; G01N 21/1702; G01N 21/47; G01N 21/55; G01N 21/9501; G02B 6/35; G02B 6/3512; G02B 6/3582; G02B 6/359; G02B 6/3598
See application file for complete search history.

(56) References Cited

U.S. PATENT DOCUMENTS 5,748,318 A   5/1998   Maris et al.
5,844,684 A   12/1998  Maris et al.
(Continued)

FOREIGN PATENT DOCUMENTS

WO   WO 02/50509 A2    6/2002
WO   WO 03/008939 A1   1/2003
WO   WO 2008/013909 A2  1/2008

OTHER PUBLICATIONS

International Search Report from International Application No. PCT/US2012/022911 mailed May 30, 2012.
(Continued)

*Primary Examiner* — Michael P Stafira
(74) *Attorney, Agent, or Firm* — Merchant & Gould, P.C.

(57) ABSTRACT

An automatically adjustable method for use in opto-acoustic metrology or other types of metrology operations is described. The method includes modifying the operation of a metrology system that uses a PSD style sensor arrangement. The method may be used to quickly adjust the operation of a metrology system to ensure that the data obtained therefrom are of the desired quality. Further, the method is useful in searching for and optimizing data that is or can be correlated to substrate or sample features or characteristics that of interest. Apparatus and computer readable media are also described.

11 Claims, 7 Drawing Sheets

(51) Int. Cl.
  *G01N 21/55* (2014.01)
  *G01N 21/47* (2006.01)
  *G01N 21/17* (2006.01)
  *G01N 21/95* (2006.01)

(56) References Cited

U.S. PATENT DOCUMENTS

| | | |
|---|---|---|
| 7,019,845 B1 | 3/2006 | Leary et al. |
| 2005/0046835 A1 | 3/2005 | Olschewski |
| 2006/0072120 A1* | 4/2006 | Leary et al. .................. 356/502 |
| 2006/0072185 A1 | 4/2006 | Proksch et al. |
| 2007/0020785 A1 | 1/2007 | Bruland et al. |
| 2007/0133086 A1* | 6/2007 | Wilhelm et al. .............. 359/385 |
| 2009/0244516 A1 | 10/2009 | Mehendale et al. |
| 2009/0279090 A1 | 11/2009 | Wolf et al. |

OTHER PUBLICATIONS

Austrian Search Report and Written Opinion for Application No. 2013057682 mailed Dec. 12, 2014.

* cited by examiner

POSITION SENSITIVE DETECTION OPTIMIZATION

This application is a National Stage Application of PCT/US2012/022911, filed 27 Jan. 2012, which claims benefit of U.S. Ser. No. 61/462,154, filed 28 Jan. 2011 and which applications are incorporated herein by reference. To the extent appropriate, a claim of priority is made to each of the above disclosed applications.

TECHNICAL FIELD

The exemplary embodiments of this invention relate generally to optical metrology methods and apparatus and, more specifically, relate to optimization of position sensitive detection for optical techniques that characterizing samples.

BACKGROUND

Optical metrology systems, for example, a opto-acoustic metrology system, can measure changes in reflectivity of the specimen that are due to a piezoreflective effect caused by ultrasonic waves propagating within the specimen. It can also measure the deflection of a laser beam due to the deformation caused by the ultrasonic waves. This type of metrology system, as well as other types known to those skilled in the art, use sensors that use position sensitive detection. These sensors detect a position and/or an intensity of a light spot in one or two-dimensions on a sensor surface. These sensors, referred to as "PSD sensors" may be either isotropic or discrete sensors. Further, PSD sensors may have one or more sensitive regions or cells.

In some opaque film metrology embodiments, multiple PSD sensors are used to measure film thickness. One such metrology system is the opto-acoustic system whose basic function is described in U.S. Pat. No. 5,748,318, the subject matter of which is incorporated by reference herein in its entirety.

In general, the opto-acoustic system measures the change in reflectivity ($\Delta R$) of a specimen that is caused by the piezoreflective effect. The piezoreflective effect is modified by detect ultrasonic waves that travel within the specimen. See FIG. 1.

As shown, a pump beam 10 is directed at the surface 16 of the sample 14. The pump beam 10 causes rapid expansion in the surface 16 as shown by bump 15. This rapid expansion creates a shock or stress wave that is dispersed into the sample 14. The initial stress wave and the components thereof that return to the surface 16 of the sample 14 cause a change in the reflectivity of the surface 16 sample 14. A probe beam 12 is directed onto and reflected from sample 14. The reflected probe beam is incident upon a sensor 20 such as a PSD sensor that detects changes in the reflectivity of the surface based on changes in the reflected probe beam.

In addition, the system shown in FIG. 1 can also measure the deflection of a probe beam 12 that is caused by the same stress waves. As can be appreciated from the nature of the bump 15, as stress waves propagating within the sample 16 intersect the surface 16, they can cause a deformation in the surface 16. A split-cell detector 20 may be used to measure the deflection in the probe beam 12 caused by deformations in the surface 16 by measuring an imbalance in the incident probe power between the two cells of detector. See FIG. 2.

Typical PSD style sensors output two types of information. The first type is position sensitive information which relates a position of an incident spot of light (e.g. probe beam laser). As perturbations in the sample surface may deflect a probe beam incident upon the surface of a sensor, deflections of the probe beam may provide information about certain characteristics of the sample. The second type of information relates to the overall radiant power or flux incident upon the sensor. The amount of power incident upon the active surface of a sensor may provide information about certain characteristics of the sample. Therefore, taken alone or together and/or as a function of some other variable such as time, the types of information provided by PSD style sensors can be used to determine characteristics of the sample under test.

PSD style sensors and the metrology systems that use them must be manually aligned and maintained. Accordingly, it can be quite time consuming to modify the operation of a metrology tool to monitor a new product or feature. Where manual modification of sensor settings is required, it is often the case that these settings are not modified, thereby preventing one from discovering new applications for the metrology tool or making it difficult to truly dial in the sensitivity of a metrology tool to obtain optimal results.

Accordingly, there is a need for an automatically adjustable sensor mechanism for use in opto-acoustic metrology or other types of metrology operations.

BRIEF SUMMARY OF THE INVENTION

In semiconductor manufacturing processes, it is imperative to ensure that the metrology tools being used to monitor the process are capable of handling the myriad types of devices that pass through a manufacturing line. Further, it is important to ensure that these metrology tools are flexible enough to capture data that is correlated with features or characteristics that are of interest both now and in the future. The present invention meets these needs by offering an automated method of modifying the operation of a metrology system that uses a PSD style sensor arrangement. The automated system may be used to quickly adjust the operation of a metrology system to ensure that the data obtained therefrom are of the desired quality. Further, an automated system such as that described hereinbelow is useful in searching for and optimizing data that is or can be correlated to substrate or sample features or characteristics that of interest now or in the future.

BRIEF DESCRIPTION OF THE DRAWINGS

The foregoing and other aspects of embodiments of this invention are made more evident in the following Detailed Description, when read in conjunction with the attached Drawing Figures, wherein:

FIG. 4b illustrates a simplified diagram of embodiment illustrated in FIG. 4a;

DETAILED DESCRIPTION

Optimizing a metrology system involves properly aligning and adjusting a sensor that captures data that includes information about a substrate or sample that is under test in a metrology system. One type of metrology system to which the present invention may be put is an opto-acoustic metrology system marketed by Rudolph Technologies, Inc. of Flanders, N.J. under the trademark METAPULSE®. Other types of metrology systems and laboratory equipment may also benefit by the application of the present invention.

In one very basic form, the present invention is embodied in an adjustable wave front splitter or divider that can change the amount of radiant power that is incident on one of a plurality of sensitive cells of a sensor. In one embodiment, the wave front splitter apportions and adjusts the incident radiant power over and across the respective cells of a two cell PSD. Other types of sensors that provide similar output to a PSD may also be used.

A movable wave front splitter may be used to adjust the amount of the probe beam that is incident on the separate elements of the split-cell detector. Various exemplary embodiments in accordance with this invention include a wave front splitter adapted to selectively balance the power of light incident on the two or more sensor elements. The opto-acoustic system may also be configured to identify, isolate, or amplify signal components within the probe beam signal returned from a specimen using the split-cell detector having a wave front splitter.

Figure 1:
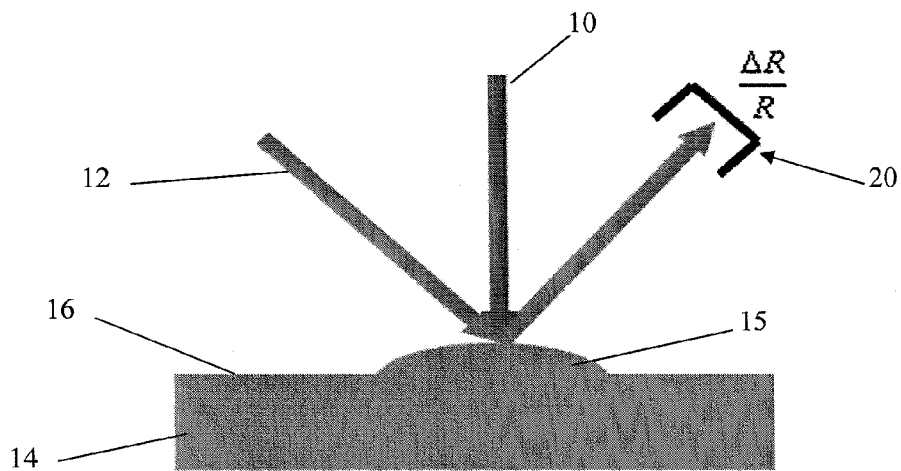
FIG. 1 illustrates a simplified diagram of a pump-pulse system configured to measure a change in reflectivity of a sample.
Figure 2:
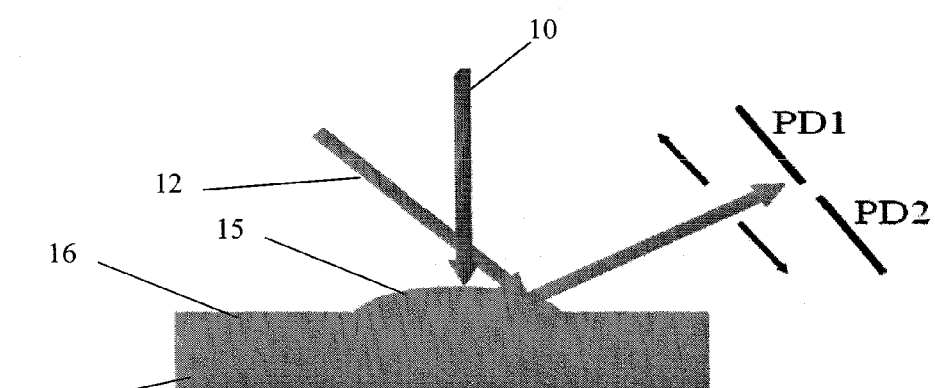
FIG. 2 illustrates a simplified diagram of a pump-pulse system configured to measure an imbalance in the incident probe beam power.
Figure 3:
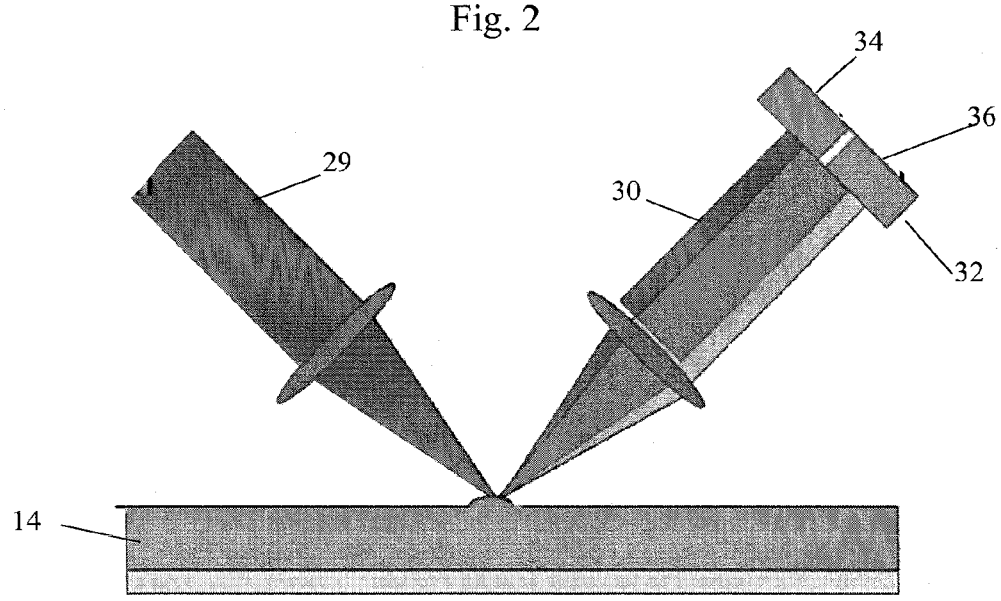
FIG. 3 illustrates a simplified diagram of a device that is suitable for use in practicing the exemplary embodiments of this invention.

FIG. 3 illustrates schematically one embodiment of the present invention. As shown, beam of light 29 is incident upon a sample. The beam of light 29 interacts with the sample so as to encode at least some characteristics of the sample in a reflected beam 30 of light that is directed onto at least a first cell 34 and a second cell 36 of a split-cell detector 32. Note that the principles of the present invention may also be applied to detectors having three or more cells. The reflected beam 30 may be evenly spread between the two cells 34, 36 to generate an approximately equal spread or radiant power across the two cells. Alternatively the beam 30 may be balanced between the cells 34, 36 in different proportions (included all on one cell and none on the other).

The resulting signal from the detector 32 carries information regarding a number of contributing factors that are of immediate interest and may also contain information that correlates with features or characteristics that have not yet been identified. Some contributions to the signal from sensor 32 include surface deformations (e.g., those caused by a strain generated in the sample), gradients in dielectric properties caused by stress, temperature and/or electronic excitation, differential reflectivity and thermal background. The combination of the signal components derived from each of the respective cells 34 and 36 depends on the application to which the system as a whole is put.

An automated sensor balancing system makes it possible to vary the ratio of the radiant flux or power split between the two cells 32, 34. For example, a wave splitter 50 (FIG. 4) may be moved (e.g., with a motorized stage as shown by arrow 54) to alter the ratio of the power (P1) sent to a first cell 32 and the power (P2) sent to a second cell 34. Such a wave front splitter may be a movable mirror of suitable characteristics that is placed in the optical path of a probe beam 30 of light that is returned from the surface of the specimen. In some embodiments the wave front splitter may be moved vertically such that the respective elements of a split-cell detector experience a different incident power depending on the position of the wave front splitter. In all instances, the splitter moves with respect to the beam 30 so as to optically split or divide the beam 30 into at least two portions.

An automatically adjustable wave front splitter may be used to quickly change the apportionment of radiant power over the cells of a sensor to achieve one of a plurality of static settings known to a user of a system to be useful for performing metrology on a particularly type of specimen or sample that is under test. Alternatively, the position of the wave front splitter, and hence the apportionment of radiant power across the cells of a sensor may be dynamically modified during one or more measurement operations, the position of the wave front splitter and the resulting apportionment ratios being recorded as each measurement is captured. The data obtained from dynamic modifications such as those described may be used to determine new correlations between data output by the metrology system and features or characteristics of a sample that is under test. Dynamic modification may also be used for periodic automatic calibration routines or for optimizing the output of a metrology sensor using common regression or other data analysis techniques.

Figure 4A:
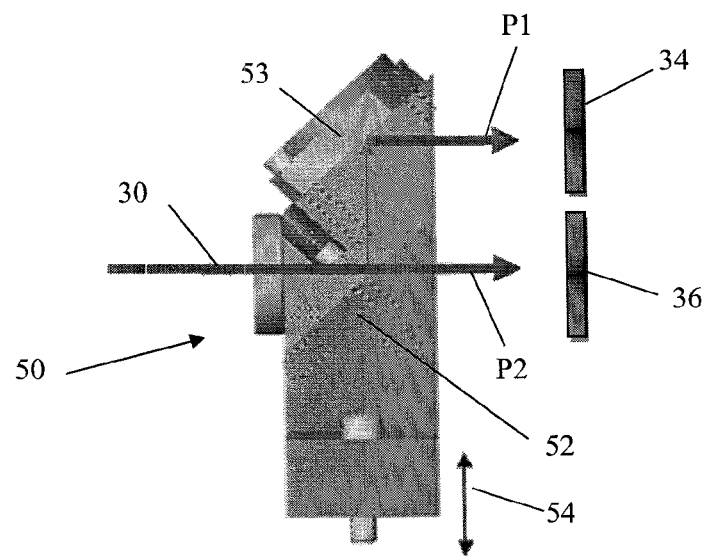
FIG. 4a illustrates a simplified diagram of the device that is suitable for use in practicing the exemplary embodiments of this invention.

FIG. 4a illustrates schematically one embodiment of a device 50 that is suitable for use in practicing the principles of this invention. As shown, a beam 30 of light enters a wave splitter 50 and is split into two beams. One beam (P1) is directed at a first cell 34 of a split cell detector and the other beam (P2) is directed at a second cell 36 of the split cell detector 32. Beam 30 is split into beams P1 and P2 by a mirror 52 positioned in the optical path of beam 30. That portion of the beam 30 that is incident on the mirror 52 will be reflected out of the path of beam 30 and onto the path of beam P1. By moving the wave splitter 50 laterally with respect to the beam 30, different areas of the mirror 52 are addressed to the beam 30, thereby changing the proportion of radiant power sent to one cell with respect to the proportion of power sent to the other cell.

Figure 4B:
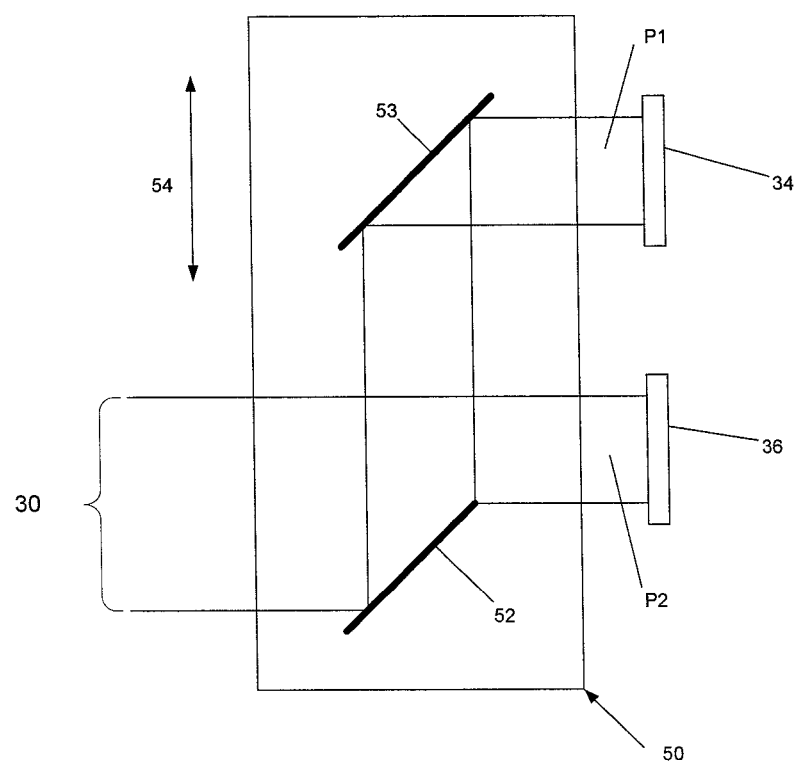

FIG. 4b is a schematic representation of the wave splitter 50 showing the mirror 52 deflecting approximately 50% of beam 30 onto the path of beam P1. Beam P1 is reflected from mirror 53 and is then incident on active cell 34 of a sensor, in this case a PSD sensor. The balance of the beam 30 not initially incident on the mirror 52 continues along its optical path as beam P2 and is incident on active cell 36 of a sensor, in this case the same PSD sensor as cell 34.

In the illustrated embodiment the position of the mirror 52 with respect to optical path of the beam 30 divides the beam 30 into two beams having radiant powers P1 and P2, respectively. The mirror 52 of the wave splitter 50 and the mirror 53 may be moved by an actuator (represented by arrow 54) between at least two positions. The first position of the wave splitter 50 results in an apportionment of substantially all of the radiant power of beam 30 being directed along the optical path of the beam indicated by radiant power P1. The second position of the wave splitter 50 results in an apportionment of substantially all of the radiant power of beam 30 being directed along the optical path of the beam indicated by radiant power P2. Actuator 54 may also position the wave splitter 50 between its first and second position such that a ratio of the radiant power apportioned between the respective optical paths is given by (P1−P2)/(P1+P2)<1 and/or (P2−P1)/(P1+P2)<1. Note that the use of additional optical elements such as optical fibers, for example, may result in an optical arrangement that may apportion the radiant power of beam 30 along multiple optical paths, each of which intersects one or more light sensitive cells of a sensor.

In some instances it may be desirable to further divide beams P1 and P2 to gain additional control of the apportionment of radiant power of the cells of a sensor. Such division may also provide additional benefits for determining deflection of a beam 30. In one such embodiment, beam P1 is not directly incident upon an active cell of a sensor. Rather, an additional wavefront splitter (not shown) may be arranged in place of the cell 34 shown in FIGS. 4a and 4b to further split the beam P1 as described above. The same arrangement may be put in place for beam P2. Where this is done for beams P1 and P2, beam 30 will then result in four beams that are addressed to respective active cells of one or more sensors, PSD, CCD or otherwise. Note that where multiple wavefront splitters 50 are used, these and/or the sensors working in conjunction therewith may be rotated with respect to the optical axis of beam 30 to differentiation the output of the respective sensors/cells.

Figure 4C:
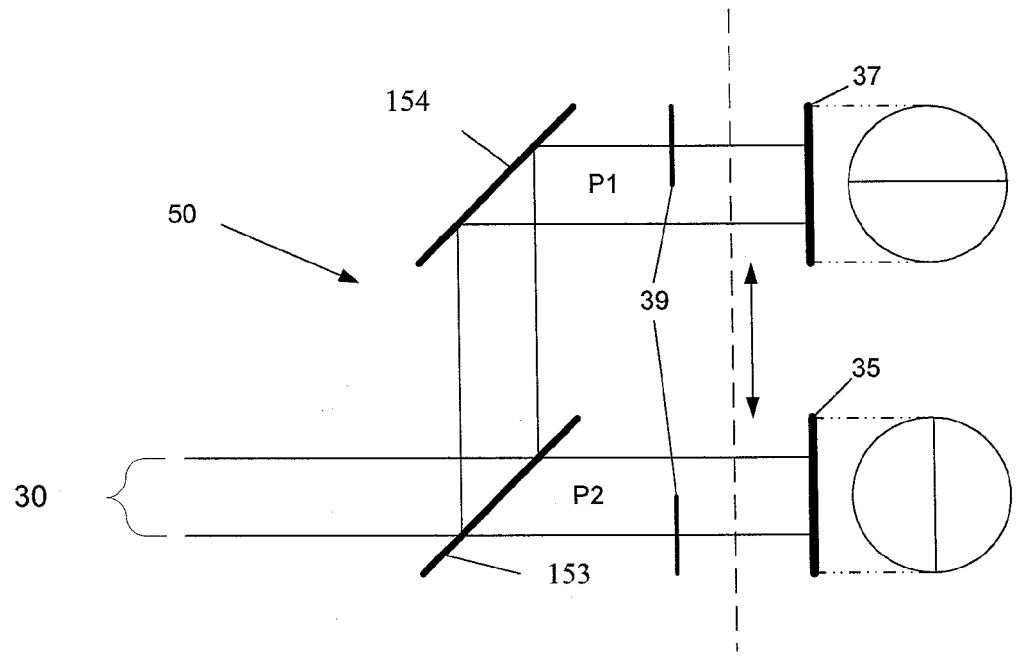
FIG. 4c illustrates a simplified diagram of the device that is suitable for use in practicing the exemplary embodiments of this invention.

The embodiment illustrated in FIGS. 4a and 4b utilized a mirror 52 to split a beam 30 into two constituent beams P1 and P2 each having a desired radiant power based on a position of the mirror 52 with respect to the beam 30. In the embodiment of FIG. 4c, mirror 52 is replaced with a pellicle beam splitter 153. In this embodiment, beam P2 continues on the optical path of beam 30 to sensor 35. In order to apportion the radiant power of beam 30 between sensors 35 and 37, stops 39 may be positioned in the paths of beams P1 and P2. Note that the stops 39 are shown schematically in FIG. 4c and may be positioned so as to block a portion of beam P1 or P2 from being incident upon sensors 37 and 35, respectively, when the sensors 35, 37 are moved relative to the wavefront splitter 50. Arrow 51 denotes the relative motion that apportions radiant power betweens sensors 35 and 37 but does not require motion of the sensors or the wavefront splitter 50.

In some embodiments the wave front splitter and beam 30 may move in relation to stationary sensors 35, 37. In other embodiments only the stops 37 will move while the wavefront splitter 50 and the sensors 35, 37 remain stationary. In yet other embodiments the sensors 35, 37 may move. In yet another embodiment, the stops may be adjustable irises that stop down the radiant power of the respective beams P1, P2. In still other embodiments, the stops 39 may be beam conditioning devices such as LCD devices that can be placed in the path of a beam to spatially filter the beam.

Note also, that if sensors 35 and 37 are active cells of larger sensors such as a PSD, the function of the embodiments in FIGS. 4a/4b and that illustrated in FIG. 4c should be substantially the same. However, if the sensors 35 and 37 are multi-cell sensors themselves (e.g. bi-cell as shown in the illustration, these multi-cell versions of sensor 35, 37 may be oriented in different angular positions with respect to the optical axes of beams P2 and P1 respectively. In this way, a quad cell sensor arrangement in which the user may effectively apportion the radiant power between four active cells instead of two is achieved.

Figure 4D:
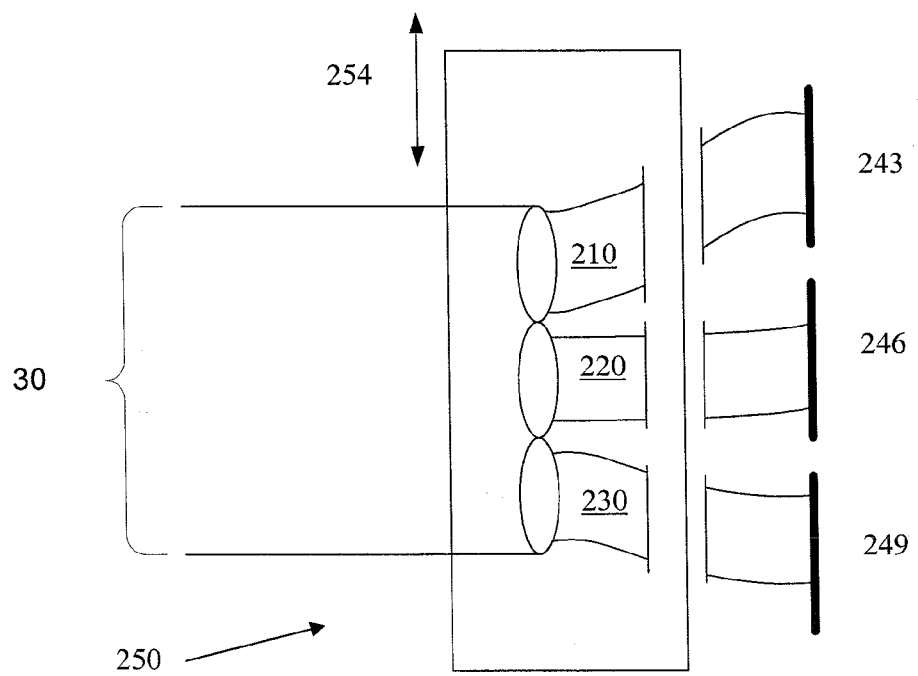
FIG. 4d illustrates a simplified diagram of the device that is suitable for use in practicing the exemplary embodiments of this invention.

FIG. 4d is a schematic representation of another wave splitter 250. As shown, the wave splitter 250 includes a plurality of fiber optic element 210, 220 and 203. A fiber optic element may be an individual fiber optic cables or a combination of fiber optic cables. The fiber optic elements 210, 220 and 230 are placed in the path of beam 30. The portion of light incident on a given fiber optic element is then directed by the cable to a sensor. For example, fiber optic element 210 may direct light to sensor 243, fiber optic element 220 may direct light to sensor 246 and fiber optic element 230 may direct light to sensor 249. The wave splitter 250 may also include an actuator 254 which may be used to move the wave splitter 250, for example, to change the fiber optic elements in the path of beam 30.

In some embodiments fiber optic elements 210, 220 and 230 may each direct light to different sensors. In another embodiment, various fiber optic elements may direct light to the same sensor. In some embodiments the wave front splitter 250 and beam 30 may move in relation to stationary sensors 243, 246 and 249. In other embodiments the sensors 243, 246 and 249 may move. The sensors 243, 246 and 249 may be active cells of larger sensors such as a PSD or may be multi-cell sensors themselves.

Figure 5:
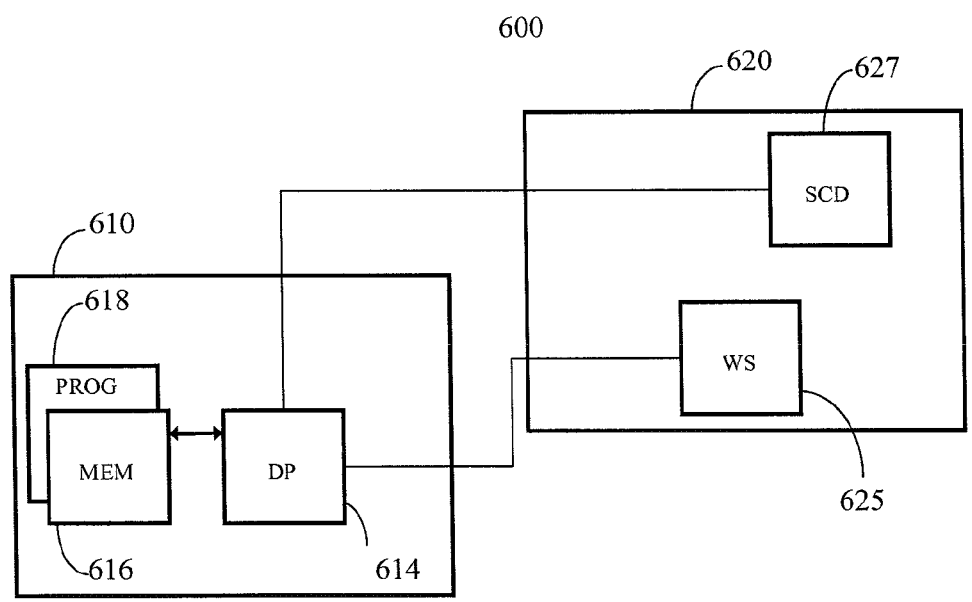
FIG. 5 shows a simplified block diagram of exemplary electronic devices that are suitable for use in practicing various exemplary embodiments of this invention.

FIG. 5 shows a simplified block diagram of an exemplary metrology system 600 that is suitable for use in practicing various exemplary embodiments of this invention. As indicated above, other metrology and laboratory equipment or systems may benefit from the application of the present invention. The optical metrology system includes an opto-acoustic system 620. The opto-acoustic system 620 includes various subsystems, such as a wave front splitter (WS) 625 and a split-cell detector (SCD) 627. Connected to the opto-acoustic system 620 is a computer system 610.

The computer system 610 includes a controller, such as a computer or a data processor (DP) 614, a computer-readable memory medium embodied as a memory (MEM) 616 that stores a program of computer instructions (PROG) 618. The DP 614 is configured to communicate with the WS 625 and the SCD 627. For example, the DP 614 may be configured to send instructions to the WS 625 in order to adjust the ratio of power split by the WS 625.

The opto-acoustic system 620 may also include beam modification elements between the WS 625 and the SCD 627. For example, a polarizer filter (not shown) may be used to modify the portion of the deflected beam directed at a first cell of the SCD 627. Lenses, filters, stops and/or other beam modification elements may be used as necessary.

Figure 6A:
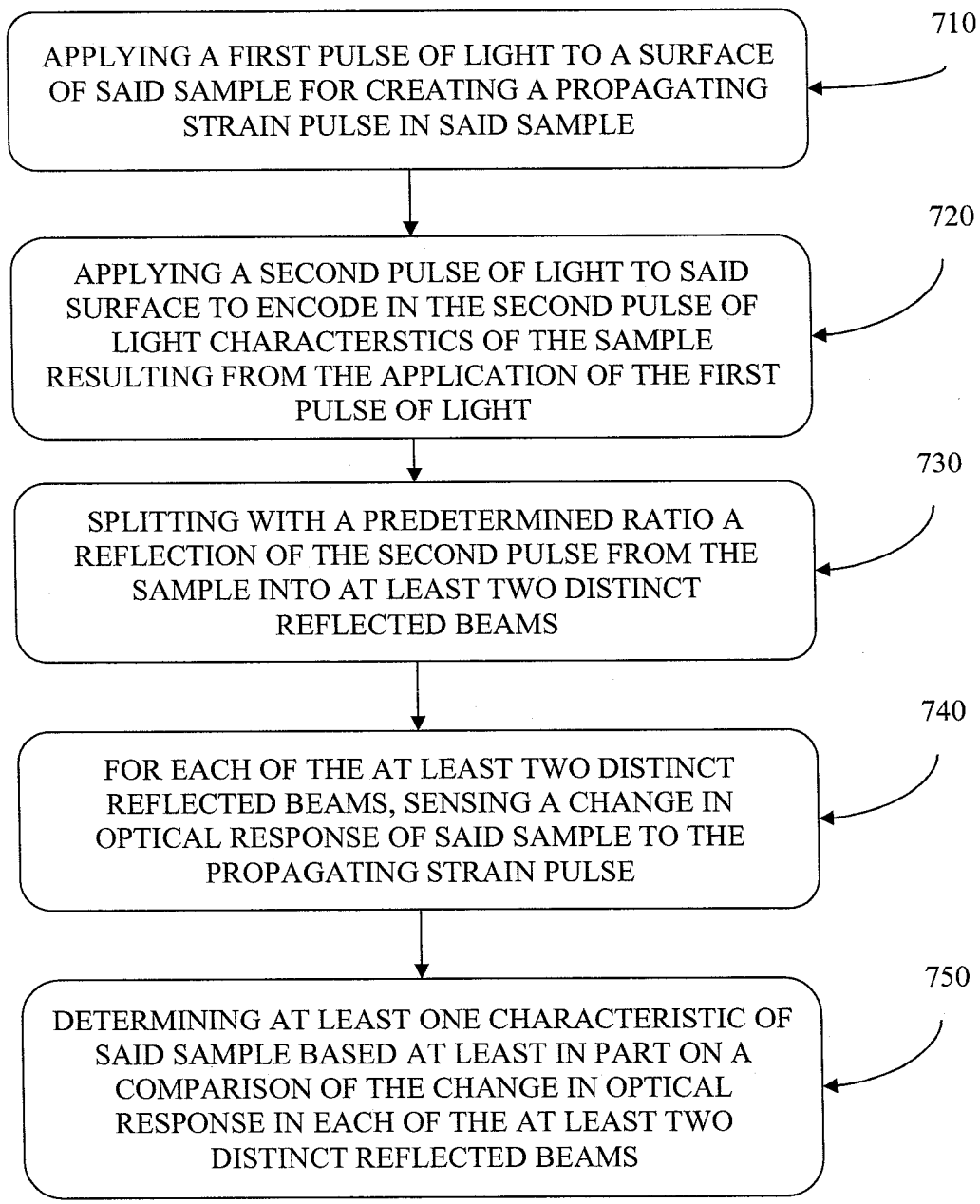
FIGS. 6a and 6b are logic flow diagrams that illustrate the operation of exemplary methods.

FIG. 6a is a chart that illustrates one method for optimizing a metrology system in accordance with exemplary embodiments of the invention. In accordance with these exemplary embodiments a method performs, at Block 710, a step of applying a first pulse of light to a surface of said sample for creating a propagating strain pulse in said sample. A second pulse of light is applied to said surface so that said second pulse of light encodes in the pulse of light information about the interaction of the propagating strain pulse with the sample at Block 720. At Block 730, a step of splitting with a predetermined ratio a reflection of the second pulse from the sample into at least two distinct reflected beams is performed. A step of sensing, for each of the at least two distinct reflected beams, a change in optical response of said sample to the propagating strain pulse is performed at Block 740. At Block 750, a step of determining at least one characteristic of said sample based at least in part on a comparison of the change in optical response in each of the at least two distinct reflected beams is performed.

Figure 6B:
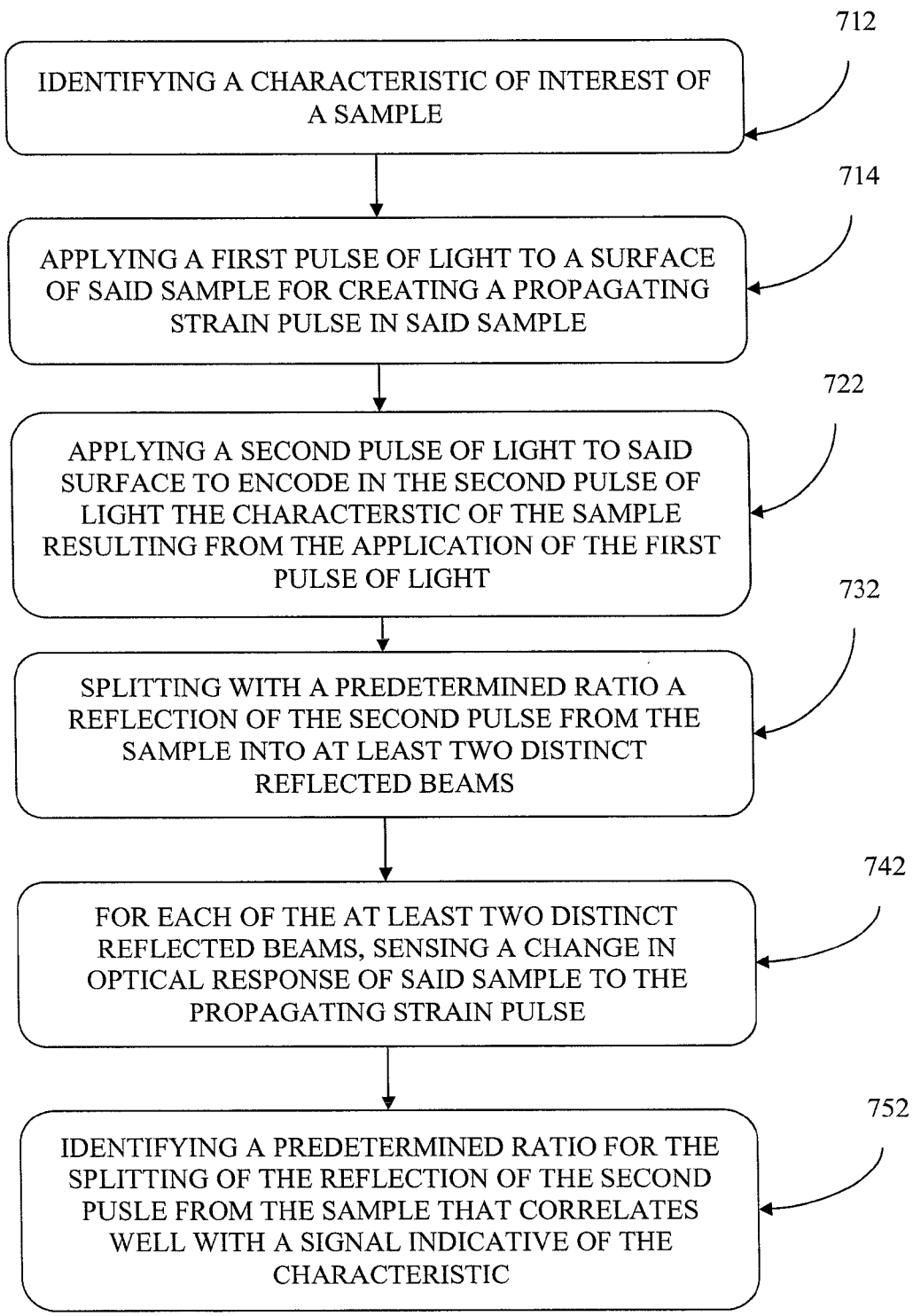

FIG. 6b is a logic flow diagram that illustrates the operation of a method for optimization of position sensitive detection for optical techniques that characterize samples, in accordance with the exemplary embodiments of this invention. In accordance with these exemplary embodiments a method performs, at Block 712 a user of the system identifies a characteristic of a sample that is to be determined. At block 714, a step of applying a first pulse of light to a surface of said sample for creating a propagating strain pulse in said sample. A second pulse of light is applied to said surface to encode information correlated to the characteristic identified at block 712. In the present embodiment, the information is encoded as a result of the strain pulse propagating in the sample; however, blocks 714 and 722 may be collapsed into a single step where only a single beam of light is required to obtain the encoded information. In either case, the present invention will have a beam of light interact with a structure of the sample itself and/or changes in the structure caused by a propagating strain pulse or in said sample as at Block 722. At Block 732, a step of splitting with a predetermined ratio a reflection of the second pulse from the sample into at least two distinct reflected beams is performed. A step of sensing a change in optical response of said sample to the propagating strain pulse or due to the structure of the sample is performed for each of the at least two distinct reflected beams, at Block 742. At Block 752, a step of determining at least one characteristic of said sample based at least in part on a comparison of the change in optical response in each of the at least two distinct reflected beams is performed.

The various blocks shown in FIGS. 6a and 6b may be viewed as method steps, and/or as operations that result from operation of computer program code, and/or as a plurality of coupled logic circuit elements constructed to carry out the associated function(s).

In another embodiment, the split ratio or apportionment of the reflected light beam may be varied with respect to any of a number of characteristics encoded in the reflected light beam due to its interaction with a sample or substrate. Correlated relationships between sensed data and the split ratio may be identified as possible characteristics of interest of the sample. The signals obtained from a reference sample may be plotted as a function of power distribution between top and bottom cells (P1/P2) starting with the whole beam on the top cell (P1) and moving the wave front splitter until the whole beam is on the bottom cell (P2).

An exemplary embodiment in accordance with this invention is a method for characterizing a sample. The method includes applying a first pulse of light to a surface of the sample for creating a propagating strain pulse in the sample. A second pulse of light is applied to the surface so that the second pulse of light interacts with the propagating strain pulse in the sample. A reflection of the second pulse from the sample is split with a predetermined ratio into at least two distinct reflected beams. The method also includes, for each of the at least two distinct reflected beams, sensing a change in optical response of the sample to the propagating strain pulse. At least characteristic of the sample is determined based at least in part on a comparison of the change in optical response in each of the at least two distinct reflected beams.

Figure 7:
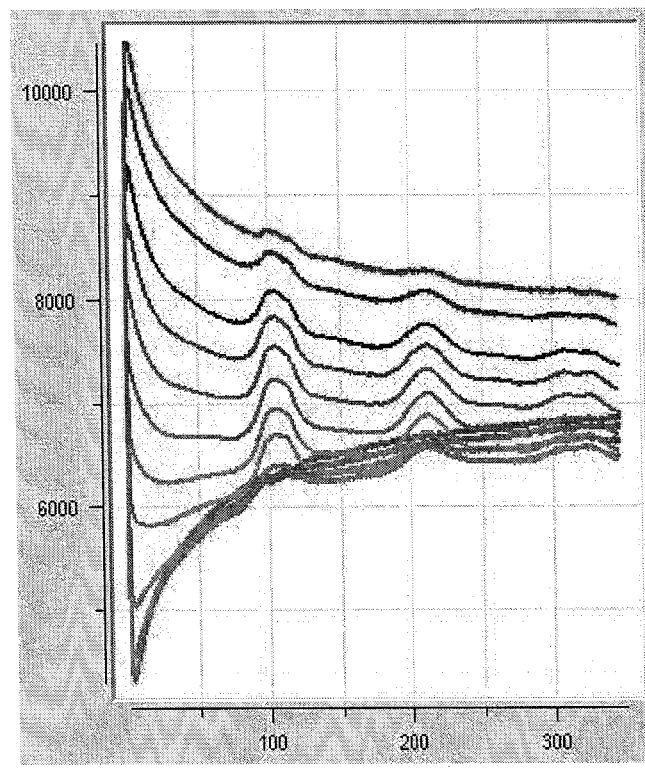
FIG. 7 illustrates PSD signals on a reference sample plotted as a function of power distribution; and, FIG. 8 illustrates reflectivity signals on the reference sample of FIG. 8 plotted as a function of power distribution.

FIG. 7 illustrates one example of data obtained from a reference sample plotted as a function of power distribution between the individual cells of a two cell PSD sensor. The uppermost curve represents a power distribution of substantially 100% power on one cell (P1) of a two cell PSD sensor. The lowest curve represents a power distribution of substantially 100% power on the remaining cell (P2) of a two cell PSD sensor. The curves falling between the uppermost and lowest curves represent various split ratios that fall between the aforementioned boundaries. The nominal power distribution ratios for these curves can be characterized as $(P1-P2)/(P1+P2)<1$, as suggested above. Biasing or unevenly apportioning a probe beam across the cells of a sensor will, without calibration, may cause bias in the output of a multi-cell sensor wherein the output signal is depending upon a difference between the outputs of the respective cells. Calibrating the sensor at its biased arrangement provides the correct position information whilst providing the benefit of optimizing signal to noise ratios with respect to selected signal characteristics.

As shown, the power distribution impacts both the magnitude and form of various features in the signal plot. In one embodiment, information correlated to a characteristic of a sample is obtained by analyzing variation in the obtained information. For example, output from a PSD style sensor operating in a position sensitive mode as shown in FIG. 7 forms a generally regular curve over time. Perturbations in this general curvature are, in at least one embodiment, indicative of deflection of a probe beam of light reflected from a sample. The width, height, and shape of these perturbations may in some embodiments provide directly information about a sample or may be used to compute, correlate or otherwise determine indirectly information about the sample. As the response curves illustrated in FIG. 7 also clearly show differences due at least in part to the apportionment of the radiant power of the reflected beam of light over the cells of the sensor, one can appreciate how one might capture information at several different apportionments or split ratios to determine directly or compute an optimal split ratio for a given application.

Figure 8:
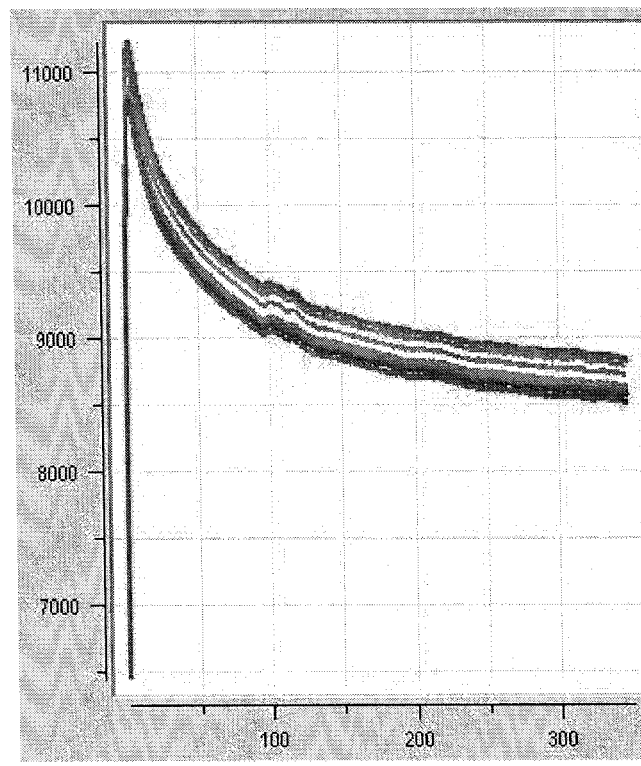

FIG. 8 illustrates reflectivity signals obtained from a two cell sensor of the same type from which the information illustrated in FIG. 7 was obtained. The uppermost curve represents a power distribution of substantially 100% power on one cell (P1) of a two cell PSD sensor. The lowest curve represents a power distribution of substantially 100% power on the remaining cell (P2) of a two cell PSD sensor. The curves falling between the uppermost and lowest curves represent various split ratios that fall between the aforementioned boundaries. The nominal power distributions represented by the intermediate curves can be characterized as follows: $(P1-P2)/(P1+P2)<1$.

In addition to using position/deflection data or reflectivity data alone to quantify a desired characteristic, it is possible to use these types of information together to more accurately and repeatably quantify the desired results. In this context, each type of information may be obtained at the same or at a different apportionment of radiant power. In some embodiments, this approach may assist in differentiating structural features of a sample such as layers in a film stack for certain applications which is not possible with one type of data alone.

Many different types of data analysis may be performed on the signals obtained from a multi-cell sensor of a metrology system that embodies the principles of the present invention. In one embodiment (opto-acoustic), subtraction of the background signal may be performed to highlight the change in the signal profile for the PSD signal as a function of power distribution between two cells. A comparison of the position signal with the reflectivity signal on the same sample shows additional features in the position signal for certain split cell configurations. In other embodiments, changes in the slope of the background signal (e.g., due to a thermal component) from a reference sample may be determined as a function of the ratio of powers between the split cells. In yet other embodiments, a signal profile from a thin copper seed barrier (CSB) wafer can be altered depending on the split power ratio. This may be used for modeling thin multi-layers. A similar behavior is apparent on various other wafers.

An exemplary embodiment in accordance with this invention is a method for optimizing signal to noise ratio in an optical sensor. The method includes directing a beam of light onto a surface of a sample such that at least one characteristic of the sample is encoded in the beam of light as it interacts with the surface of the sample. The beam of light is at least partially reflected from the surface of the sample. The method also includes directing the reflected beam of light onto an optical sensor having at least two discrete light sensitive surfaces. The method includes modifying an apportionment of radiant power of the reflected beam of light between the at least two discrete light sensitive surfaces. The method also includes obtaining information from the optical sensor that is at least partially based on both the apportionment of radiant power between the at least two discrete light sensitive surfaces and at least one of the characteristics of the sample encoded in the reflected beam of light. The method includes determining based at least in part on the information the at least one characteristic of the sample.

In a further exemplary embodiment of the method above, the method also includes iteratively adjusting the apportionment of radiant power between the at least two discrete light sensitive surfaces and, for each adjustment, determining based at least in part on the information the at least one characteristic of the sample. The method includes determining an optimal apportionment of radiant power between the at least two discrete light sensitive surfaces for the at least one characteristic of the sample.

In a further exemplary embodiment of any one of the methods above, the method also includes a priori identifying the at least one characteristic of the sample that is to be determined and subsequently identifying an optimal apportionment of radiant power between the at least two discrete light sensitive surfaces for the at least one characteristic of the sample.

In a further exemplary embodiment of any one of the methods above, the method also includes adjusting the position of a beam splitter relative to an optical path of a reflected beam returned from a sample to apportion the reflected beam over the at least two discrete light sensitive surfaces of the optical sensor. The method may also include automatically adjusting the position of the beam splitter based on a type of the sample.

In a further exemplary embodiment of any one of the methods above, the method is performed by a processor executing a computer program tangibly encoded on a computer readable medium.

Another exemplary embodiment in accordance with this invention is a sensor adjustment mechanism for optimizing signal to noise ratio in an optical sensor. The mechanism includes a beam splitter coupled to an actuator configured to move the beam splitter relative to a beam of light. A surface of the beam splitter is configured to pass a first portion of the beam of light incident thereon along a first optical path and to reflect a second portion of the beam of light incident thereon along a second optical path. The mechanism also includes an optical sensor having a plurality of light sensitive cells. At least one of the light sensitive cells is configured to be positioned along the first optical path and configured to be responsive to the first portion of the beam of light incident thereon. At least one other light sensitive cell is configured to be positioned along the second optical path and configured to be responsive to the second portion of the beam of light incident thereon. Actuation of the beam splitter with respect to the optical path of the beam of light results in an optical arrangement in which a selected apportionment of radiant power may be made between at least the first and second light sensitive cells.

In a further exemplary embodiment of the sensor adjustment mechanism above, the beam splitter is configured to be moved by the actuator between at least a first position in which substantially all of the radiant power directed onto the optical sensor is apportioned onto the at least one light sensitive cell positioned along the first optical path and a second position in which substantially all of the radiant power directed onto the optical sensor is apportioned onto the at least one other light sensitive cell positioned along the second optical path. The beam splitter may also be configured to be moveable by the actuator to at least one position in which a radiant power (P1) incident upon the at least one light sensitive cell positioned on the first optical path and a radiant power (P2) incident upon the at least one other light sensitive cell positioned on the second optical path are related by the equation: $(P1-P2)/(P1+P2)<1$.

In another exemplary embodiment of any one of the sensor adjustment mechanisms above, the mechanism also includes an optical element positioned on the second optical path to direct light reflected from the beam splitter to the at least one other light sensitive cell positioned on the second optical path.

A further exemplary embodiment in accordance with this invention is an apparatus for optimizing signal to noise ratio in an optical sensor. The apparatus includes means for directing a beam of light onto a surface of a sample such that at least one characteristic of the sample is encoded in the beam of light as it interacts with the surface of the sample. The beam of light is at least partially reflected from the surface of the sample. The apparatus also includes means for directing the reflected beam of light onto an optical sensor having at least two discrete light sensitive surfaces. The apparatus includes means for modifying an apportionment of radiant power of the reflected beam of light between the at least two discrete light sensitive surfaces. The apparatus also includes means for obtaining information from the optical sensor that is at least partially based on both the apportionment of radiant power between the at least two discrete light sensitive surfaces and the at least one of the characteristics of the sample encoded in the reflected beam of light. The apparatus includes means for determining based at least in part on the information the at least one characteristic of the sample.

In another exemplary embodiment of the apparatus above, the modifying means comprises means for iteratively adjusting the apportionment of radiant power between the at least two discrete light sensitive surfaces. The determining means comprises means for determining for each adjustment, based at least in part on the information the at least one characteristic of the sample, and means for determining an optimal apportionment of radiant power between the at least two discrete light sensitive surfaces for the at least one characteristic of the sample.

Based on the foregoing it should be apparent that the exemplary embodiments of this invention provide a method, apparatus and computer program(s) to optimization of position sensitive detection for optical techniques that characterizing samples. Generally, various exemplary embodiments of the invention can be implemented in different mediums, such as software, hardware, logic, special purpose circuits or any combination thereof. As a non-limiting example, some aspects may be implemented in software which may be run on a computing device, while other aspects may be implemented in hardware.

Any use of the terms "connected", "coupled" or variants thereof should be interpreted to indicate any such connection or coupling, direct or indirect, between the identified elements. As a non-limiting example, one or more intermediate elements may be present between the "coupled" elements. The connection or coupling between the identified elements may be, as non-limiting examples, physical, electrical, magnetic, logical or any suitable combination thereof in accordance with the described exemplary embodiments. As non-limiting examples, the connection or coupling may comprise one or more printed electrical connections, wires, cables, mediums or any suitable combination thereof.

Various modifications and adaptations to the foregoing exemplary embodiments of this invention may become apparent to those skilled in the relevant arts in view of the foregoing description, when read in conjunction with the accompanying drawings. However, any and all modifications will still fall within the scope of the non-limiting and exemplary embodiments of this invention.

Furthermore, some of the features of the various non-limiting and exemplary embodiments of this invention may be used to advantage without the corresponding use of other features. As such, the foregoing description should be considered as merely illustrative of the principles, teachings and exemplary embodiments of this invention, and not in limitation thereof.

We claim:

1. A method for optimizing signal to noise ratio in an optical sensor comprising:
   a. directing a beam of light onto a surface of a sample such that at least one characteristic of the sample is encoded in the beam of light as it interacts with the surface of the sample, the beam of light being at least partially reflected from the surface of the sample;
   b. directing the reflected beam of light onto an optical sensor having at least two discrete light sensitive surfaces;
   c. modifying an apportionment of radiant power of the reflected beam of light between the at least two discrete light sensitive surfaces;
   d. obtaining information from the optical sensor that is at least partially based on the apportionment of radiant power between the at least two discrete light sensitive surfaces and at least partially based on at least one of the characteristics of the sample encoded in the reflected beam of light; and,
   e. determining based at least in part on the information the at least one characteristic of the sample.

2. The method of claim 1 further comprising:
   a. iteratively adjusting the apportionment of radiant power between the at least two discrete light sensitive surfaces and, for each adjustment, determining based at least in part on the information the at least one characteristic of the sample; and,
   b. determining an optimal apportionment of radiant power between the at least two discrete light sensitive surfaces for the at least one characteristic of the sample.

3. The method of claim 1 further comprising:
   a. identifying a priori the at least one characteristic of the sample that is to be determined; and,
   b. subsequently identifying an optimal apportionment of radiant power between the at least two discrete light sensitive surfaces for the at least one characteristic of the sample.

4. The method of claim 1 further comprising:
   a. adjusting the position of a beam splitter relative to an optical path of a reflected beam returned from a sample to apportion the reflected beam over the at least two discrete light sensitive surfaces of the optical sensor.

5. The method of claim 4 further comprising:
   a. automatically adjusting the position of the beam splitter based on a type of the sample.

6. A sensor adjustment mechanism comprising:
   a. a beam splitter coupled to an actuator configured to move the beam splitter relative to a beam of light, where a surface of the beam splitter is configured to pass a first portion of the beam of light incident thereon along a first optical path and to reflect a second portion of the beam of light incident thereon along a second optical path; and
   b. an optical sensor having a plurality of light sensitive cells, at least one of the light sensitive cells configured to be positioned along the first optical path and configured to be responsive to the first portion of the beam of light incident thereon and at least one other light sensitive cell configured to be positioned along the second optical path and configured to be responsive to the second portion of the beam of light incident thereon;
   c. where actuation of the beam splitter with respect to the optical path of the beam of light results in an optical arrangement in which a selected apportionment of radiant power may be made between at least the first and second light sensitive cells.

7. The sensor adjustment mechanism of claim 6 where the beam splitter is configured to be moved by the actuator between at least a first position in which substantially all of the radiant power directed onto the optical sensor is apportioned onto the at least one light sensitive cell positioned along the first optical path and a second position in which substantially all of the radiant power directed onto the optical sensor is apportioned onto the at least one other light sensitive cell positioned along the second optical path.

8. The sensor adjustment mechanism of claim 7 where the beam splitter configured to be moveable by the actuator to at least one position in which a radiant power (PI) incident upon the at least one light sensitive cell positioned on the first optical path and a radiant power (P2) incident upon the at least one other light sensitive cell positioned on the second optical path are related by the equation: $(P1-P2)/(P1+P2)<1$.

9. The sensor adjustment mechanism of claim 6 further comprising:
   a. an optical element positioned on the second optical path to direct light reflected from the beam splitter to the at least one other light sensitive cell positioned on the second optical path.

10. An apparatus for optimizing signal to noise ratio in an optical sensor comprising:
    a. means for directing a beam of light onto a surface of a sample such that at least one characteristic of the sample is encoded in the beam of light as it interacts with the surface of the sample, the beam of light being at least partially reflected from the surface of the sample;
    b. means for directing the reflected beam of light onto an optical sensor having at least two discrete light sensitive surfaces;
    c. means for modifying an apportionment of radiant power of the reflected beam of light between the at least two discrete light sensitive surfaces;
    d. means for obtaining information from the optical sensor that is at least partially based on the apportionment of radiant power between the at least two discrete light sensitive surfaces and at least partially based on at least one of the characteristics of the sample encoded in the reflected beam of light; and
    e. means for determining based at least in part on the information the at least one characteristic of the sample.

11. The apparatus of claim 10,
    a. where the modifying means comprises means for iteratively adjusting the apportionment of radiant power between the at least two discrete light sensitive surfaces,
    b. where the determining means comprises means for determining for each adjustment, based at least in part on the information the at least one characteristic of the sample, and means for determining an optimal apportionment of radiant power between the at least two discrete light sensitive surfaces for the at least one characteristic of the sample.

* * * * *